(12) United States Patent
Park et al.

(10) Patent No.: US 12,104,195 B2
(45) Date of Patent: *Oct. 1, 2024

(54) REELIN/VEGF-C PRODUCTION/ACTIVATION PROMOTER AND SKIN EXTERNAL COMPOSITION USING THE SAME

(71) Applicant: Amorepacific Corporation, Seoul (KR)

(72) Inventors: Phil June Park, Yongin-si (KR); Hyunsoo Kim, Yongin-si (KR); Dong Hyun Kim, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/326,505

(22) Filed: May 31, 2023

(65) Prior Publication Data

US 2023/0383330 A1 Nov. 30, 2023

(30) Foreign Application Priority Data

May 31, 2022 (KR) .................. 10-2022-0067018

(51) Int. Cl.
| | | |
|---|---|---|
| *A61K 8/64* | (2006.01) | |
| *A61K 36/258* | (2006.01) | |
| *A61K 38/17* | (2006.01) | |
| *C07K 16/22* | (2006.01) | |
| *C12P 21/00* | (2006.01) | |

(52) U.S. Cl.
CPC .............. *C12P 21/005* (2013.01); *A61K 8/64* (2013.01); *A61K 36/258* (2013.01); *A61K 38/1709* (2013.01); *C07K 16/22* (2013.01); *A61K 2800/85* (2013.01)

(58) Field of Classification Search
None
See application file for complete search history.

(56) References Cited

U.S. PATENT DOCUMENTS

2023/0381091 A1   11/2023   Kim et al.

FOREIGN PATENT DOCUMENTS

| EP | 2 859 918 A1 | 4/2015 | |
|---|---|---|---|
| JP | 2008-189609 A | 8/2008 | |
| JP | 2012-236795 A | 12/2012 | |
| KR | 20120092229 A * | 8/2012 | ............. A61K 36/00 |
| KR | 10-2015-0057664 A | 5/2015 | |
| KR | 10-1578581 B1 | 12/2015 | |
| KR | 10-2019-0024203 A | 3/2019 | |
| KR | 10-2020-0022940 A | 3/2020 | |
| KR | 10-2085115 B1 | 3/2020 | |
| KR | 10-2247551 B1 | 5/2021 | |
| KR | 10-2441009 B1 | 9/2022 | |
| WO | 2016/035182 A1 | 3/2016 | |

OTHER PUBLICATIONS

Sunwoo, H. H., et al. Biotechnol. Lett. (2013), 35; 1017-1022.*
Sophie Lutter et al., "Smooth muscle-endothelial cell communication activates Reelin signaling and regulates lymphatic vessel formation", J. Cell Biol., 2012, pp. 837-849, vol. 197, No. 6.
Alejandra González-Loyola et al., "Development and aging of the lymphatic vascular system", Advanced Drug Delivery Reviews, 2021, pp. 63-78, vol. 169.
Jie Yu et al., "Ginsenoside Rg1 enhances lymphatic transport of intrapulmonary silica via VEGF-C/VEGFR-3 signaling in silicotic rats", Biochemical and Biophysical Research Communications, 2016, pp. 182-188, vol. 472.
Kaedeko Fukada et al., "Antiedema effects of Siberian ginseng in humans and its molecular mechanism of lymphatic vascular function in vitro", Nutrition Research, 2016, pp. 689-965, vol. 36.
Tianyu Sun et al., "Gypenoside XVII protects against spinal cord injury in mice by regulating the microRNA-21-mediated PTEN/AKT/mTOR pathway", International Journal of Molecular Medicine, 2021, pp. 1-11, 48, 146.
Ji Yeon Lee et al.. , "Anti-dermatitic effect of fermented ginseng extract including rich compound K through inhibiting activation of macrophage", Food Sci Biotechnol, 2019, pp. 1845-1852, 28(6).
Zhipeng Li et al., "Effects of fermented ginseng root and ginseng berry on obesity and lipid metabolism in mice fed a high-fat diet", Journal of Ginseng Research, 2018, pp. 312-319, vol. 42.
Na Rae Shin et al., "Anti-Obesity Effect of Fermented Panax notoginseng Is Mediated via Modulation of Appetite and Gut Microbial Population", Frontiers in Pharmacology, Jul. 2021, pp. 1-16, vol. 12, Article 665881.
Myung Joo Han et al., "Effects of Red and Fermented Ginseng and Ginsenosides on Allergic Disorders", biomolecules, 2020, pp. 1-17, 10, 634.

(Continued)

*Primary Examiner* — Bong-Sook Baek
(74) *Attorney, Agent, or Firm* — Sughrue Mion, PLLC

(57) ABSTRACT

Provided are a reelin and/or VEGF-C production and/or activation promoter including a compound represented by Chemical Formula 1 and/or a ginseng extract containing the compound, as an active ingredient, and a skin external composition including the same.

[Chemical Formula 1]

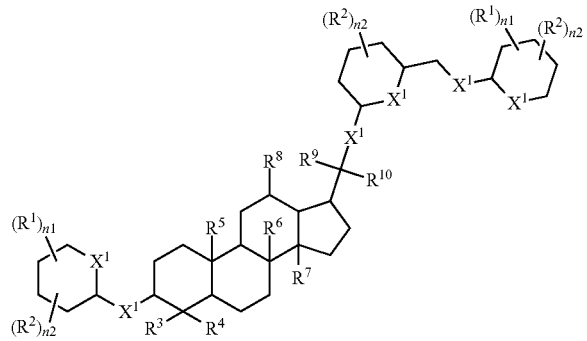

In Chemical Formula 1, each substituent is as defined in the specification.

3 Claims, 6 Drawing Sheets

(56) References Cited

OTHER PUBLICATIONS

Sang Ah Yi et al., "Fermented ginseng extract, BST204, disturbs adipogenesis of mesenchymal stem cells through inhibition of S6 kinase 1 signaling", Journal of Ginseng Research, 2020, pp. 58-66, vol. 44.
Yingli Yu et al., "Gypenoside XVII protects against myocardial ischemia and reperfusion injury by inhibiting ER stress-induced mitochondrial injury", Journal of Ginseng Research, 2021, pp. 642-653, vol. 45.
Korean Notice of Allowance for 10-2022-0067018, dated Jul. 26, 2022.
Wikipedia, https://en.wikipedia.org/wiki/Ginseng, last visited Feb. 1, 2024.

\* cited by examiner

REELIN/VEGF-C PRODUCTION/ACTIVATION PROMOTER AND SKIN EXTERNAL COMPOSITION USING THE SAME

CROSS-REFERENCE TO RELATED APPLICATION

This application claims priority to and the benefit of Korean Patent Application No. 10-2022-0067018 filed in the Korean Intellectual Property Office on May 31, 2022, the entire contents of which are incorporated herein by reference.

BACKGROUND OF THE INVENTION

(a) Field of the Invention

This disclosure relates to a reelin and/or VEGF-C production and/or activation promoter and a skin external composition using the same.

(b) Description of the Related Art

Edema refers to a condition in which tissue fluid accumulates between cells of the body, and simply, is a symptom of body swelling. This also may be caused by heart disease, kidney disease, or a blood circulation disorder in any part of the body. Particularly, since legs of the body are distant from the heart and are largely affected by gravity, blood flow to the heart decreases, which causes edema. In addition, women may experience edema during normal pregnancy or preeclampsia, and when lots of moisture or salt is taken or when fatigued or unable to sleep, the edema may temporarily appear but will subside on its own. When capillary permeability is increased, for example, in case of burns, trauma, local inflammation, allergic reaction, and the like, the edema may locally occur. In particular, leg edema accompanies swelling of feet and ankles and thus may be easily recognized as a feeling of tight shoes, and in addition, since a swollen feeling of the legs accompanies a heavy feeling of the legs, fatigue of the whole body may be perceived as the leg edema. Systemic edemas may be classified into cardiac, renal, hepatic, endocrine, and dystrophic edemas, and local edemas may be classified into edema due to occlusion of blood vessels and lymphatic vessels, vasomotor edema, etc. When the edema develops, there may be body swelling, weight gain, swollen eyes when waking up from sleep, tight rings on fingers, and tight shoes. When calf tibia is pressed with a finger, it may appear hollow and as a pitted edema. Edema is known to promote blood circulation disorders and skin aging due to local excessive moisture in the skin. In general, skin problems are known to exacerbate conditions of people having improper lymphatic functions and overloaded lymphedema.

The skin is in the closest contact with an external environment in the human body and is an important organ protecting the inside of the human body therefrom. The skin is largely classified into epidermis, dermis, and hypodermis. Herein, the hypodermis consists of fat cells forming adipose tissues storing energy as fat and playing a role of accumulating or releasing energy in the body. In other words, the hypodermis is stored as triglycerides in adipocytes, when more energy is supplied than demanded, it is broken into free fatty acids and glucose when the energy is depleted.

On the other hand, recently in contemporary society, with improvement of living standards according to economic growth, the obese population is rapidly increasing due to lack of exercise and a high protein diet, so more people are suffering from many diseases due to obesity. Accordingly, exercise therapy, diet therapy, drug therapy, etc. are being developed and conducted to treat the obesity in contemporary society.

However, the exercise therapy and the diet therapy may not be expected to have an appropriate effect on the obesity and obesity-related diseases of contemporary people who are busy with life, and moreover, fat cells, when they are once made, may be reduced in size but are not naturally removed and permanently remain in the body. Accordingly, it may be appropriate to develop and use safe skin external preparations (e.g., ointments, cosmetics, and the like) that can help break down fat to accompany the therapies.

Therefore, the present inventors confirmed that a specific wormwood extract promotes production or activation of reelin and/or VEGF-C as an active ingredient, and further, thereby improves swelling, lymphedema, skin wrinkles, and obesity, completing the present invention.

SUMMARY OF THE INVENTION

An embodiment is to provide a promoter that promotes reelin and VEGF-C production or activation.

Another embodiment provides a skin external composition using the promoter.

Another embodiment provides a method for improving swelling, lymphedema, skin wrinkles, or obesity by applying the skin external composition to the skin.

According to an embodiment, a reelin and/or VEGF-C production and/or activation promoter includes a compound represented by Chemical Formula 1 and/or ginseng extract containing the compound as an active ingredient.

[Chemical Formula 1]

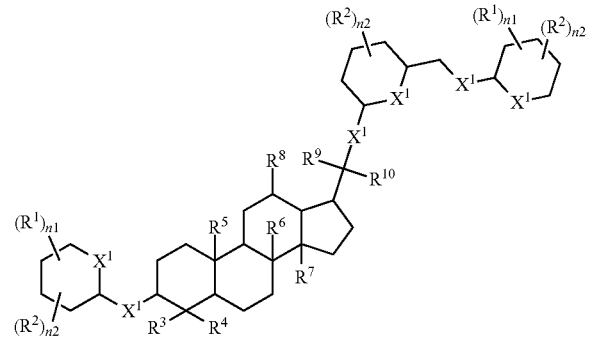

In Chemical Formula 1, $X^1$ is an oxygen atom or a sulfur atom, $R^1$ to $R^{10}$ are each independently a hydroxy group or a substituted or unsubstituted C1 to C20 alkyl group, and n1 and n2 are each independently an integer of 0 to 4, provided that $1 \leq n1$ and $n2 \leq 4$.

The ginseng extract may be a fermented ginseng extract.

In Chemical Formula 1, $R^1$ may be a C1 to C20 alkyl group substituted with a hydroxy group, $R^2$ and $R^8$ are each independently a hydroxy group, $R^3$ to $R^7$ and $R^9$ may each independently be an unsubstituted C1 to C20 alkyl group, $R^{10}$ may be a C1 to C20 alkyl group substituted with a functional group represented by Chemical Formula 2, n1 may be an integer of 1, and n3 may be an integer of 3,

[Chemical Formula 2]

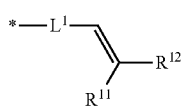

wherein, in Chemical Formula 2, $L^1$ may be a substituted or unsubstituted C1 to C20 alkylene group, and $R^{11}$ and $R^{12}$ may each independently be a hydrogen atom or a substituted or unsubstituted C1 to C20 alkyl group.

Chemical Formula 1 may be represented by Chemical Formula 1-1.

[Chemical Formula 1-1]

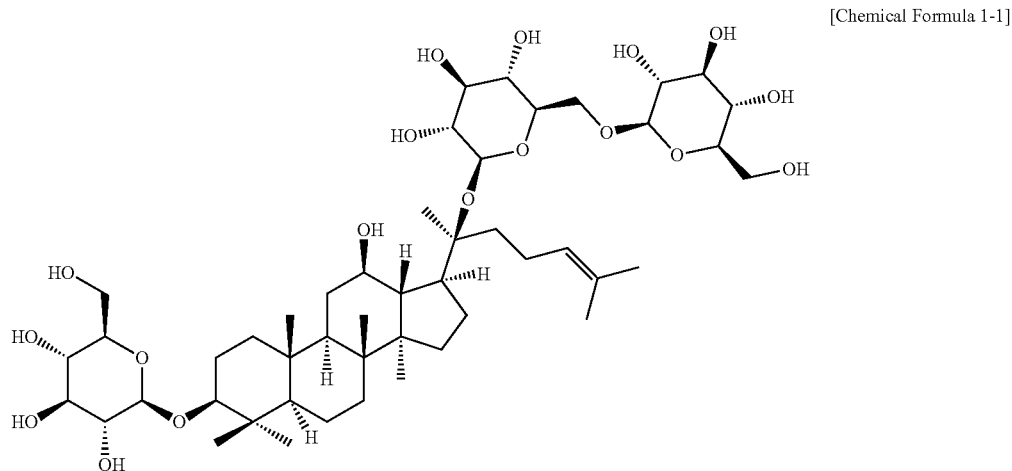

The ginseng extract including the compound represented by Chemical Formula 1 may be included in a concentration range of about 1 μg/ml to about 100 mg/ml based on the reelin and/or VEGF-C production and/or activation promoter.

The compound represented by Chemical Formula 1 may be included in a concentration range of about 50 nmoles to about 5000 nmoles based on the reelin and/or VEGF-C production and/or activation promoter.

Another embodiment provides a skin external composition for improving swelling, lymphedema, skin wrinkles, or obesity, which includes the compound represented by Chemical Formula 1 and/or ginseng extract containing the compound, as an active ingredient, by promoting the reelin and/or VEGF-C production and/or activation.

The skin external composition may be an agent for improving swelling, and the swelling may be caused by abnormal formation of lymphatic vessels, dysfunction of lymphatic vessels, or both.

The skin external composition may be an agent for improving lymphedema, and the lymphedema may be caused by an abnormal formation of lymphatic vessels, dysfunction of lymphatic vessels, or both.

The skin external composition may be an anti-obesity agent, and the obesity may be caused by an abnormal formation of lymphatic vessels, dysfunction of lymphatic vessels, or both.

Another embodiment provides a method for improving swelling, lymphedema, skin wrinkles, or obesity by applying the skin external composition.

According to an embodiment, provided is a novel ingredient effective for preventing or controlling swelling, lymphedema, wrinkle formation, or obesity by inducing the expression of reelin and/or VEGF-C to activate the lymphatic function.

DETAILED DESCRIPTION OF THE EMBODIMENTS

Figure 1:
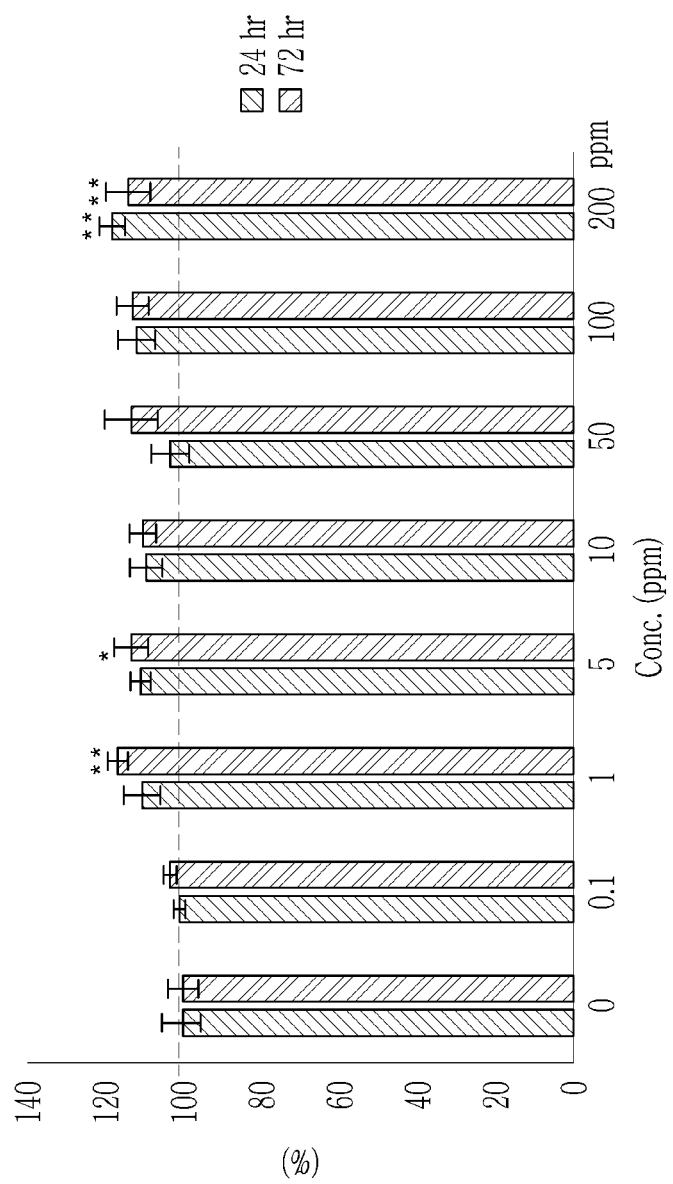
FIG. 1 is a graph showing the results of cytotoxicity test of fermented ginseng extract in lymphatic cells.

Hereinafter, example embodiments of the present invention will be described in detail. However, these example embodiments are only examples and do not limit the present invention. However, this disclosure may be embodied in many different forms and is not construed as limited to the example embodiments set forth herein.

As used herein, the term "reelin (RELN)" refers to an extracellular matrix-related molecule.

As used herein, when specific definition is not otherwise provided, "substituted" refers to replacement of at least one hydrogen of a functional group of the present invention by at least one substituent selected from a halogen atom (F, Br, Cl, or I), a hydroxy group, a nitro group, a cyano group, an amino group ($NH_2$, $NH(R^{200})$, or $N(R^{201})(R^{202})$, wherein $R^{200}$, $R^{201}$, and $R^{202}$ are the same or different and are each independently a C1 to C10 alkyl group), an amidino group, a hydrazine group, a hydrazone group, a carboxyl group, a substituted or unsubstituted alkyl group, a substituted or unsubstituted alkenyl group, a substituted or unsubstituted alkynyl group, a substituted or unsubstituted alicyclic organic group, a substituted or unsubstituted aryl group, and a substituted or unsubstituted heterocyclic group.

As used herein, when specific definition is not otherwise provided, "alkyl group" refers to a C1 to C20 alkyl group, and specifically a C1 to C15 alkyl group, "cycloalkyl group" refers to a C3 to C20 cycloalkyl group, and specifically a C3 to C18 cycloalkyl group, "alkoxy group" refers to a C1 to C20 alkoxy group, and specifically a C1 to C18 alkoxy group, "aryl group" refers to a C6 to C20 aryl group, and specifically a C6 to C18 aryl group, "alkenyl group" refers to a C2 to C20 alkenyl group, and specifically a C2 to C18 alkenyl group, "alkylene group" refers to a C1 to C20 alkylene group, and specifically a C1 to C18 alkylene group, and "arylene group" refers to a C6 to C20 arylene group, and specifically a C6 to C16 arylene group.

As used herein, when a definition is not otherwise provided, the term "combination" refers to mixing or copolymerization. Also, "copolymerization" refers to block copolymerization or random copolymerization, and "copolymer" refers to a block copolymer or random copolymer.

The skin vasculature resides within the dermis and consists of blood vessels and lymphatic vessels. In order to maintain homeostasis, tissue fluid that has moved out of the blood vessel must be refluxed back into the vein. The veins of the skin efficiently send blood flow to the center. However, the veins themselves lack ability to receive tissue fluid. Accordingly, tissues receiving the tissue fluid, that is, lymphatic vessels, are also an essential structure to the skin.

The lymphatic vessels play an important role in maintaining a constant state of microenvironment around cells by recovering water and proteins that are constantly leaking from unnecessary substances and blood vessels present in the skin. In addition, the lymphatic vessels have been thought to play a role in resisting infectious agents and foreign agents from outside through transport of T lymphocytes.

The lymphatic vessels are known to have symptoms such as swelling, lymphedema, and the like, which are lymphatic dysfunctions. In addition, the lymphatic vessels are not limited to swelling but are known to play an important role in photoaging (wrinkle formation) of the skin by ultraviolet (UV) rays.

Studies so far have identified VEGFR-3 as a transmembrane receptor, which is specifically present in the lymphatic vessels, and discovered VEGF-C and VEGF-D as its ligand. VEGF-C acts on the lymphatic vessels to promote proliferation, migration, and luminal cavity formation of lymphatic endothelial cells, thereby activating functions of the lymphatic vessels. In addition, VEGF-C is introduced into edema as a pathological condition of swelling to explore possible gene therapy.

In addition, in recent years, mice with genetic mutations that cause the dysfunction of lymphatic vessels are known to show obesity when mature. With respect to a mechanism that formation and dysfunction of lymphatic vessels indicate obesity, lymph fluid flowing through the lymphatic vessels is known to promote differentiation of progenitor mast cells into fat. In other words, the lymphatic fluid has been reported to leak out of the lymphatic vessels due to dysfunction of the lymphatic vessels and thus differentiate the fat and furthermore form obesity. Accordingly, a VEGF-C promoter is expected as a therapeutic agent to prevent obesity that functionally regenerates the lymphatic vessels.

VEGF family genes exist from VEGF-A to VEGF-E. Among them, VEGF-B and VEGF-E have been identified as factors acting on blood vessels alone. VEGF-A is known to be present in the skin and act on the lymphatic vessels, but on the contrary, worsens functions of the lymphatic vessels.

In the skin, VEGF-D is reported to exist in a very small amount in the dermis, but since knockout mice of VEGF-D do not cause abnormalities in formation and function of the lymphatic vessels, VEGF-D is considered to be nonessential for the formation of the lymphatic vessels of the skin. On the other hand, mice with high expression of VEGF-C in the epidermis confirm that an increase in the number of the lymphatic vessels in the dermis indicates that VEGF-C in the skin is strongly expressed in the epidermis. As a result of blocking an effect of VEGF-C in the epidermis by highly expressing a neutralizing antibody of VEGFR-3, a receptor of VEGF-C, the number of lymphatic vessels in the dermis has been dramatically reduced (Makinen, T., Jussila, L., Veikkola, T., Karpanen, T., Kettunen, M. I., Pulkkanen, K. J., Kauppinen, R., Jackson, D. G., Kubo, H., Nishikawa, S., Yla-Herttuala, S. & Alitalo, K. 2001 Nat Med 7, 199-205). Accordingly, since functions of the lymphatic vessels in the skin dermis are controlled by VEGF-C expressed in the epidermis, VEGF-C is blocked from functioning, resulting in swelling (edema).

Furthermore, in recent years, various attempts have been made to control swelling or edema by activating or strengthening lymph or lymphatic vessels to control swelling or edema, improve skin aging (wrinkles), and prevent, suppress, and treat obesity, wherein the activation or strengthening of the lymph or the lymphatic vessels may also be achieved by promoting production, differentiation, and activity of reelin in addition to VEGF-C.

Accordingly, the present inventors performed numerous experiments and trials and errors to find an active ingredient capable of improving swelling, lymphedema, skin wrinkles, or obesity by promoting the production or activity of reelin and/or VEGF-C and confirmed that a composition including a compound represented by Chemical Formula 1 obtained from a ginseng extract, specifically a fermented ginseng extract and/or a fermented ginseng extract including the compound as an active ingredient may function as a reelin and/or VEGF-C production and/or activation promoter, completing the present invention.

[Chemical Formula 1]

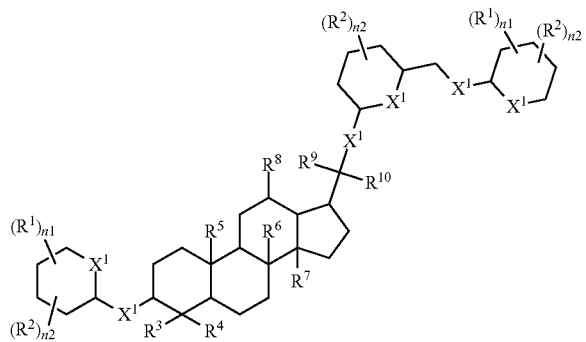

In Chemical Formula 1, $X^1$ is an oxygen atom or a sulfur atom, $R^1$ to $R^{10}$ are each independently a hydroxy group or a substituted or unsubstituted C1 to C20 alkyl group, and n1 and n2 are each independently an integer of 0 to 4, provided that $1 \leq n1+n2 \leq 4$.

The compound represented by Chemical Formula 1 may be obtained from a fermented ginseng extract but not from an unfermented (or before fermentation) ginseng extract, for example, a fresh ginseng extract. The present inventors, after studying functionality of ginseng extracts for several years, have confirmed for the first time that fermented ginseng extracts exhibit significantly increased productivity of reelin and/or VEGF-C, compared with unfermented ginseng extracts, and also, that secretion of the reelin and/or VEGF-C may be stimulated to activate lymphatic vessels and ultimately improve skin swelling and the like, completing the present invention.

Although various efficacies of the ginseng extracts are known, all ginseng extracts have no effective effect on preventing or controlling swelling, lymphedema, wrinkle formation, or obesity, and so far, attempts to release health functional foods containing a small amount of simple ginseng extracts, for example, fresh ginseng extract, to use ginseng extracts for muscle or respiratory diseases, or the

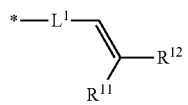

[Chemical Formula 2]

wherein, in Chemical Formula 2,
$L^1$ may be a substituted or unsubstituted C1 to C20 alkylene group, and
$R^{11}$ and $R^{12}$ may each independently be a hydrogen atom or a substituted or unsubstituted C1 to C20 alkyl group.

For example, Chemical Formula 1 may be represented by Chemical Formula 1-1.

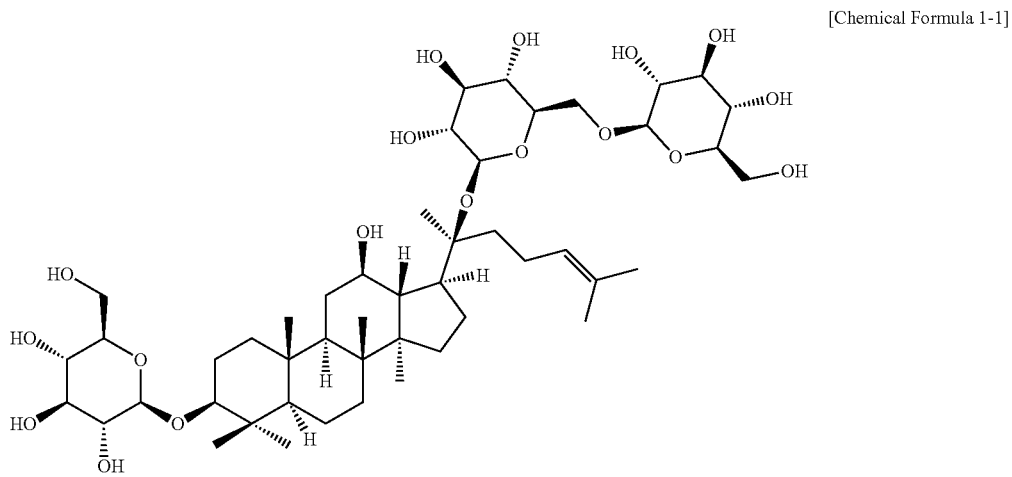

[Chemical Formula 1-1]

like, but no attempts to use fermented ginseng extracts as a reelin and/or VEGF-C production and/or activation promoter have yet been made.

For example, the fermented ginseng extracts may be obtained by fermenting ginseng, which is performed after rolling the ginseng. In other words, the fermented ginseng extracts may be extracts obtained by fermenting the rolled ginseng. The extracts obtained by fermenting the rolled ginseng may be more appropriately used as a reelin and/or VEGF-C production and/or activation promoter than extracts directly obtained from the fermented ginseng without rolling. The rolling may refer to a process of repeatedly rubbing ginseng and ginseng roots with a physical force (breaking cell tissues and cell walls).

For example, the fermented ginseng may be ginseng fermented under anaerobic conditions. Herein, this fermented ginseng under anaerobic conditions may be more appropriately used as a reelin and/or VEGF-C production and/or activation promoter than fermented ginseng under aerobic conditions.

For example, in Chemical Formula 1, $R^1$ may be a C1 to C20 alkyl group substituted with a hydroxy group, $R^2$ and $R^8$ may each independently be a hydroxy group, $R^3$ to $R^7$ and $R^9$ may each independently be an unsubstituted C1 to C20 alkyl group, $R^{10}$ may be a C1 to C20 alkyl group substituted with a functional group represented by Chemical Formula 2, n1 may be an integer of 1, and n3 may be an integer of 3, For example, the (fermented) ginseng extract including the compound represented by Chemical Formula 1 may be included in a concentration range of about 1 μg/ml to about 100 mg/ml, for example about 1 μg/ml to about 10 mg/ml, for example about 1 μg/ml to about 1 mg/ml, for example about 1 μg/ml to about 500 μg/ml, for example about 1 μg/ml to about 100 μg/ml, for example greater than or equal to about 1 μg/ml and less than or equal to about 100 μg/ml, less than or equal to about 90 μg/ml, less than or equal to about 80 μg/ml, less than or equal to about 70 μg/ml, less than or equal to about 60 μg/ml, less than or equal to about 50 μg/ml, less than or equal to about 40 μg/ml, less than or equal to about 30 μg/ml, or less than or equal to about 20 μg/ml, or for example about 1 μg/ml to about 50 μg/ml, based on the total amount of the reelin and/or VEGF-C production and/or activation promoter.

For example, the compound represented by Chemical Formula 1 may be included in a concentration range of about 50 nmoles to about 5000 nmoles, for example greater than or equal to about 50 nmoles and less than or equal to about 5000 nmoles, less than or equal to about 4500 nmoles, less than or equal to about 4000 nmoles, less than or equal to about 3500 nmoles, less than or equal to about 3000 nmoles, less than or equal to about 2500 nmoles, less than or equal to about 2000 nmoles, less than or equal to about 1500 nmoles, or less than or equal to about 1000 nmoles, or for example about 50 nmoles to about 2500 nmoles based on the total amount of the reelin and/or VEGF-C production and/or activation promoter.

The reelin and/or VEGF-C production and/or activation promoter according to an embodiment includes the compound represented by Chemical Formula 1 and/or (fermented) ginseng extract including the compound as an active ingredient, and the concentration range is satisfied, thereby effectively promoting the formation and function of lymphatic vessels. Symptoms accompanying the dysfunction of the lymphatic vessels may include not only swelling and lymphedema, but also photoaging (wrinkle formation, etc.) of the skin caused by ultraviolet rays, obesity, and the like. The reelin and/or VEGF-C production and/or activation promoter according to one embodiment of the present invention may be effective in preventing and suppressing photoaging of the skin according to ultraviolet (UV) rays and obesity along with swelling or lymphedema. In addition, the reelin and/or VEGF-C production and/or activation promoter may also be effective in treating congenital lymphedema.

The photoaging of the skin means a change in appearance and function of the skin, which is generally confirmed as a result of repeated exposure to sunlight. Ultraviolet (UV) light, a component of sunlight, and particularly, moderate UV (called UVB, a wavelength of about 290 nm to about 320 nm), mainly causes the photoaging. An exposure dose of UVB required to cause the photoaging is currently unknown. However, repeated exposure to UVB at a level causing erythema or sunburn usually leads to the photoaging. Clinically, the photoaging may be specified as skin roughness, formation of wrinkles, pigmentation of spots, haemorrhage, formation of sagging, onset of telangiectasia, occurrence of moles, onset of purpura, susceptibility to scarring, atrophy, occurrence of a fibrotic pigment removal area, and premalignant and malignant tumors. The photoaging usually occurs on skin habitually exposed to sunlight such as the face, ears, head, neck, and hands.

According to an embodiment, a skin external composition for improving swelling, lymphedema, skin wrinkles, or obesity includes the compound represented by Chemical Formula 1 and/or (fermented) ginseng extract including the compound, as an active ingredient to promote reelin and/or VEGF-C production and/or activation.

For example, the skin external composition may be a swelling improving agent, and the swelling may be caused by abnormal formation of lymphatic vessels, dysfunction of lymphatic vessels, or both.

For example, the skin external composition may be an agent for improving lymphedema and the lymphedema may be caused by an abnormal formation of lymphatic vessels, dysfunction of lymphatic vessels, or both.

For example, the skin external composition may be an anti-obesity agent, and the obesity may be caused by an abnormal formation of lymphatic vessels, dysfunction of lymphatic vessels, or both.

It is possible to appropriately determine the dosage, application form, and formulation of the skin external composition according to the embodiment according to the purpose of use. The form of application of the skin external composition is not particularly limited, and it can be applied both by inhalation and transdermally. The formulations may be any form, for example, perfumes, shampoos, conditioners, skin care, body shampoos, body conditioners, body powders, air fresheners, deodorants, bath agents, lotions, creams, soaps, toothpastes, cosmetics such as aerosol products, and other fragrances in general. It may also be used for medicines such as inhalation drugs.

In addition to the above essential ingredients, the skin external composition includes ingredients commonly used in skin external compositions, for example cosmetics and pharmaceuticals, or whitening agents, moisturizing agents, antioxidants, oily ingredients, ultraviolet absorbers, surfactants, thickeners, alcohols, powder components, colorants, aqueous components, water, various skin nutrients, and the like may be appropriately blended as needed.

In addition, metal sequestering agents such as disodium edetate, trisodium edetate, sodium citrate, sodium polyphosphate, sodium metaphosphate, and gluconic acid, caffeine, tannin, verapamil, tranexamic acid and derivatives thereof, licorice extract, glabridean, hot water extract of quince fruit, various crude drugs, drugs such as tocopherol acetate, glycyrrhizic acid, and derivatives thereof, or salts thereof, vitamin C, magnesium ascorbate phosphate, ascorbyl glucoside, arbutin, whitening agents such as kojic acid, sugars, such as glucose, fructose, mannose, sucrose, and trehalose, vitamin A such as retinoic acid, retinol, retinol acetate, and retinol palmitate, and the like may also be further suitably included.

For example, the skin external composition may be a cosmetic composition.

In the present specification "cosmetic" may refer to any material that may have a medical function in addition to the cosmetic function, as well as the cosmetic function.

The chemical formulation of the cosmetic composition is not particularly limited and may be appropriately selected as desired.

For example, the cosmetic composition may be formulated into chemical formulations such as solutions, suspend liquids, emulsions, pastes, gels, creams, lotions, powders, soaps, surfactant-containing cleansings, oils, powder foundations, emulsion foundations, wax foundations, and sprays, but is not limited thereto. More specifically, it may be formulated into cosmetic compositions such as detergents, tonics, hair dressings, nourishing lotions, essences, serums, treatments, conditioners, shampoos, lotions, wools, or hair dyes, and the like, and may be formulated into basic cosmetics such as oil-in-water (O/W) type, a water-in-oil (W/O) type, and the like. For example, the composition may have one formulation selected from skin lotions, skin toners, astringents, lotions, milk lotions, moisture lotions, nourishing lotions, massage creams, nourishing creams, moisture creams, hand creams, ointments, foundations, essences, nourishing essences, packs, soaps, cleansing foams, cleansing lotions, cleansing creams, body lotions, body cleansers, gels, cream, patches, and sprays. In addition, in the composition, in addition to the above-mentioned essential components in each chemical formulation, other components may be appropriately selected and formulated without difficulty by a person of ordinary skill in the art according to types or use purposes of other external preparations. For example, ultraviolet (UV) blocking agents, hair conditioning agents, fragrances, and the like may be further included.

The cosmetic composition may include a cosmetically acceptable medium or base. These are all chemical formulations suitable for topical applications. The cosmetic composition may be provided in the forms of emulsions obtained by dispersing an oil phase in an aqueous phase, suspensions, microemulsions, microcapsules, microgranules, or ion-type (liposome) and/or non-ionized vesicle dispersing agents, or in the forms of creams, skins, lotions, powders, ointments, sprays, or concealment sticks. These compositions may be prepared according to conventional methods in the art.

When the chemical formulation of the present invention is a solution or emulsion, a solvent, a solubilizer, or an emulsifier, it may be used as carrier components. For example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or a fatty acid ester of sorbitan may be used.

If the chemical formulation of the present invention is a suspension, the carrier component may be a diluent of a liquid such as water, ethanol, or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, tracant, and the like.

If the chemical formulation of the present invention is pastes, creams, or gels, the carrier component may be animal oil, vegetable oil, wax, paraffin, starch, tracant, cellulose derivatives, polyethylene glycol, silicone, bentonite, silica, talc, or zinc oxide.

If the chemical formulation of the present invention is powders or sprays, the carrier component may be lactose, talc, silica, aluminum hydroxide, calcium silicate, or polyamide powders. Particularly, in the case of sprays, a propellant such as chlorofluorohydrocarbon, propane/butane, or dimethyl ether may be additionally included.

In an embodiment of the present invention, it may include thickeners in addition to the cosmetic composition. The thickeners included in the cosmetic composition of the present invention may be methyl cellulose, carboxyl methyl cellulose, carboxyl methyl hydroxy guanine, hydroxy methyl cellulose, hydroxyethyl cellulose, carboxyl vinyl polymer, polyquaternium, cetearyl alcohol, stearic acid, and carrageenan. Preferably one or more of carboxyl methyl cellulose, carboxyl vinyl polymer, and polyquaternium may be used, and most preferably a carboxyl vinyl polymer may be used.

In an embodiment of the present invention, the cosmetic composition may include a variety of suitable bases and additives as needed, and the types and amounts of these components may be easily selected by the inventor. If necessary, it may include an acceptable additive, and may further include, for example, conventional ingredients such as antiseptics, pigments, additives, and the like.

The antiseptics may be specifically phenoxyethanol or 1,2-hexanediol, and the fragrances may be artificial fragrances.

In an embodiment of the present invention, the cosmetic composition may include a composition selected from water-soluble vitamins, oil-soluble vitamins, polymeric peptides, polymeric polysaccharides, sphingolipids, and seaweed extracts. Other ingredients that may be added include fats and oils, humectants, emollients, surfactants, organic and inorganic pigments, organic powders, ultraviolet (UV) absorbers, antiseptics, fungicides, antioxidants, plant extracts, pH adjusters, alcohols, pigments, fragrances, blood circulation accelerators, coolants, anhidrotics, purified water, and the like.

In addition, the compounding components which may be added other than these are not limited thereto. Moreover, any component may be blended in the range which does not damage the purpose and effect of the invention.

Furthermore, the skin external composition according to an embodiment may be used as a pharmaceutical composition.

Advantages and features of the present invention and methods for achieving them will be apparent with reference to the examples described below in detail. One aspect of the present disclosure will be described in detail with reference to examples. However, these examples are specifically provided for describing the present invention, and the range of the present invention is not limited to these examples.

EXAMPLES

Preparation Example: Preparation of Fermented Ginseng Extract and Confirmation of the Compound Represented by Chemical Formula 1-1

Fresh ginseng was washed two to three times, rolled for 30 minutes, cut/crushed into 1 cm to 2 cm pieces, then sealed (at 50° C.) and fermented for 3 weeks. Subsequently, the fermented ginseng was dried with hot air at 60° C. for one day, obtaining desired fermented ginseng.

The fermented ginseng was placed in 50% to 80% EtOH for 1 to 5 hours at 50° C. to 80° C., which was repeated 1 to 3 times for extraction. The extracted sample was filtered under a reduced pressure with a Whatman No. 1 paper filter, concentrated with a vacuum rotatory concentrator to remove solvent components, and purified, preparing a fermented ginseng extract.

Furthermore, an HPLC analysis was performed by using a column (Mightysil RP-18 GP C18) and an ultraviolet absorbance detector (203 nm) under conditions of an injection amount (10 uL), a flow rate (1.0 mL/min), and a mobile phase (D.I WATER, Acetonitrile), which showed that a compound represented by Chemical Formula 1-1 (Sigma-Aldrich Co., Ltd.) was present in the fermented ginseng extract.

[Chemical Formula 1-1]

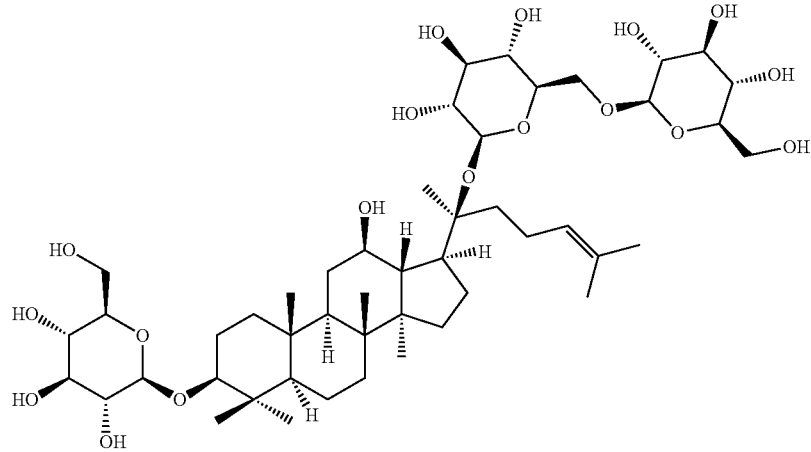

Experimental Example 1: Cytotoxicity Analysis (1) Human dermal lymphatic endothelial cells (HDLEC, PromoCell, Germany) were newly cultured in 96 well dishes for one day and then treated with the fermented ginseng extract of the preparation example at each concentration of 0 ppm (μg/ml) to 200 ppm (μg/ml). The cells were cultured for 24 hours and 72 hours, and then measured with respect to absorbance at 450 nm by using a QuantiMax WST-8 Cell viability assay kit to check cell viability, and the results are shown in FIG. 1.

Referring to FIG. 1, the wormwood extract had no cytotoxicity within a concentration range of 200 ppm.

(2) Normal human epidermal keratinocytes (NHEK, PromoCell, Germany) were newly cultured in 96 well dishes for one day, and then treated with the fermented ginseng extract of the preparation example at each concentration of 0 ppm (μg/ml) to 200 ppm (μg/ml). The treated human epidermal keratinocytes were cultured for 24 hours and 72 hours, and then measured with respect to absorbance at 450 nm by using a QuantiMax WST-8 Cell viability assay kit to check cell viability, and the results are shown in FIG. 2.

Figure 2:
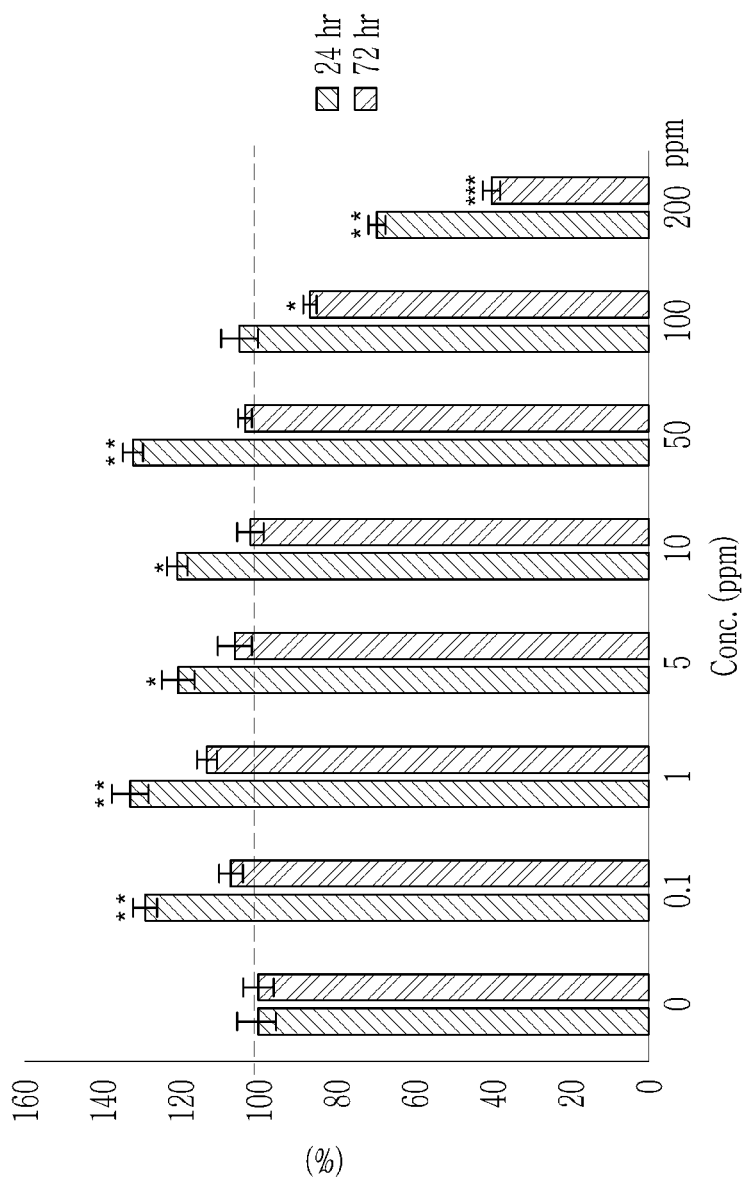
FIG. 2 is a graph showing cytotoxicity test results of the fermented ginseng extract in keratinocytes.

Referring to FIG. 2, the wormwood extract was confirmed to have no cytotoxicity within the concentration range of 50 ppm.

Experimental Example 2: Reelin Cytokine Analysis

Figure 3:
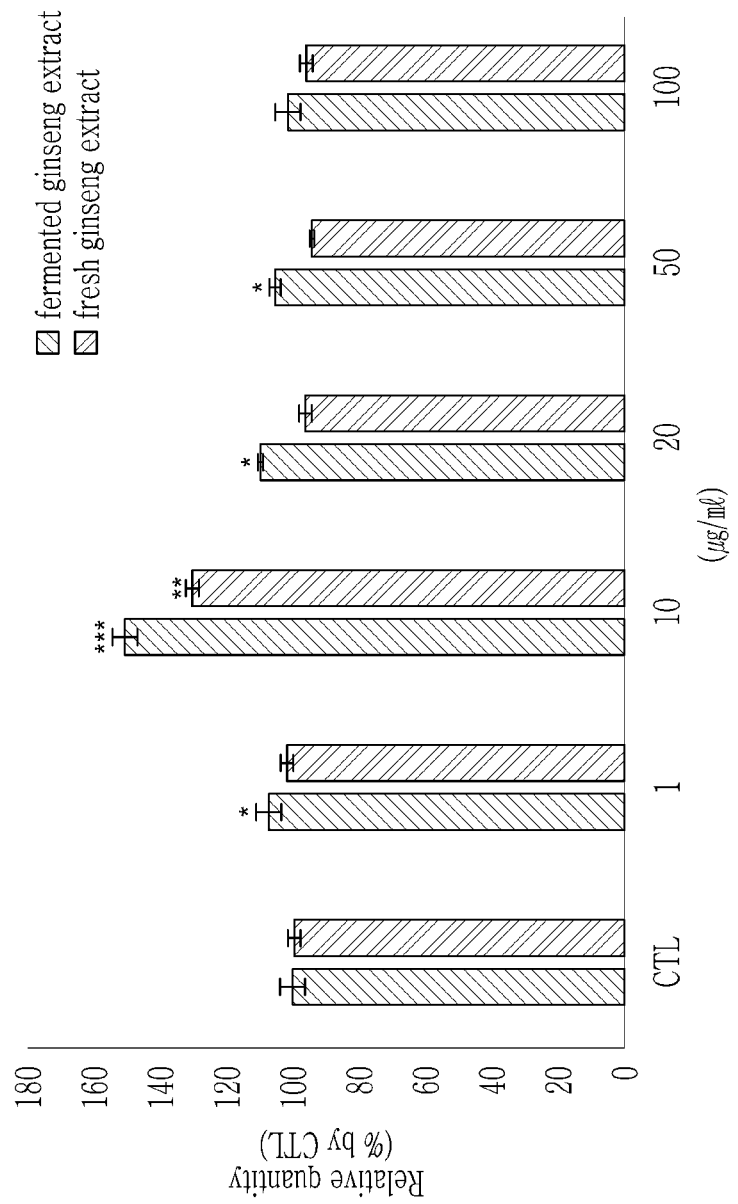
FIG. 3 is a graph showing results of reelin cytokine analysis of the fermented ginseng extract in lymphatic cells.
Figure 4:
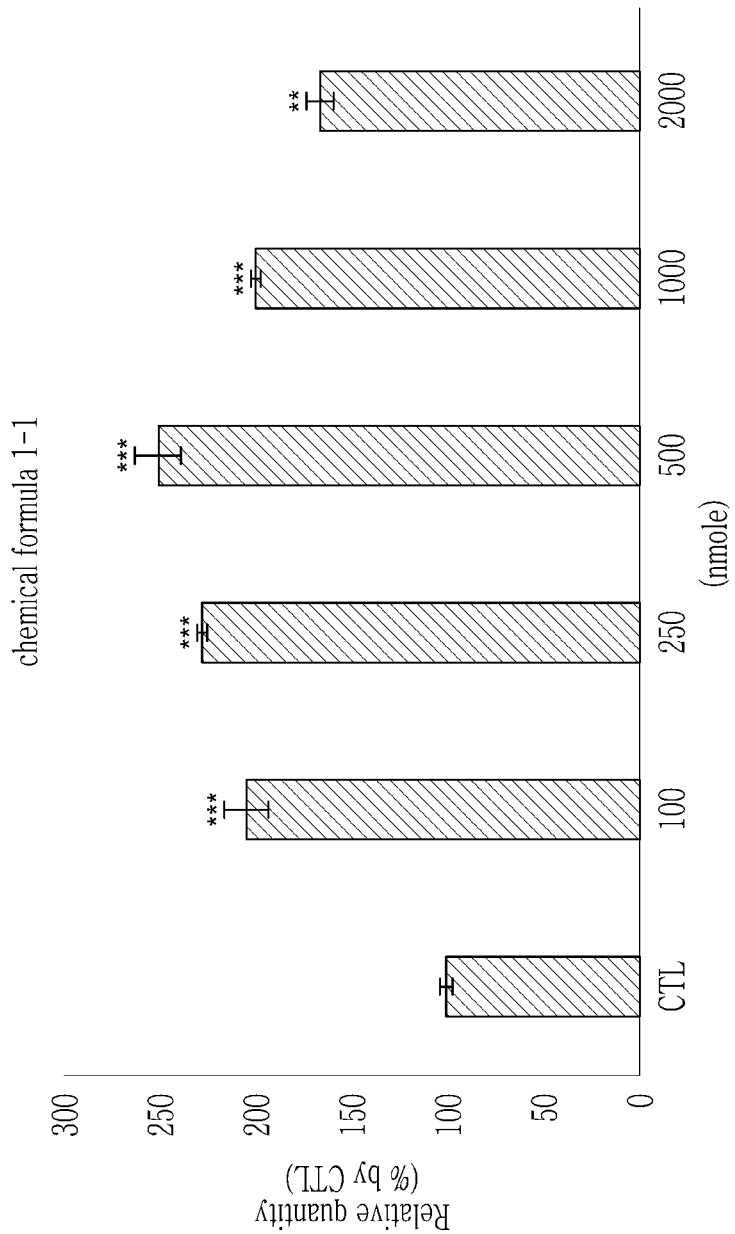
FIG. 4 is a graph showing results of reelin cytokine analysis of the compound represented by Chemical Formula 1-1 in lymphatic cells.

Human dermal lymphatic endothelial cells were cultured in 6 well plates for 24 hours, while treated with DMSO as a control group (reference; 100%), treated with the fermented ginseng extract of the preparation example and the compound represented by Chemical Formula 1-1 (Sigma-Aldrich Co., Ltd.) at each concentration of 1 μg/ml, 10 μg/ml, 20 μg/ml, 50 μg/ml, and 100 μg/ml and at each concentration of 100 nmole, 250 nmole, 500 nmole, 1000 nmole, and 2000 nmole, cultured for 48 hours, and then measured with respect to production and activity of reelin through a reelin cytokine analysis according to a manual by using Human reelin ELISA Kit (Mybiosource, Inc., U.S.A.), and the results are shown in FIGS. 3 and 4.

Referring to FIGS. 3 and 4, the compound represented by Chemical Formula 1-1 and the fermented ginseng extract including the same improved production and activity of reelin, compared with the control group.

Experimental Example 3: VEGF-C Cytokine Analysis

Figure 5:
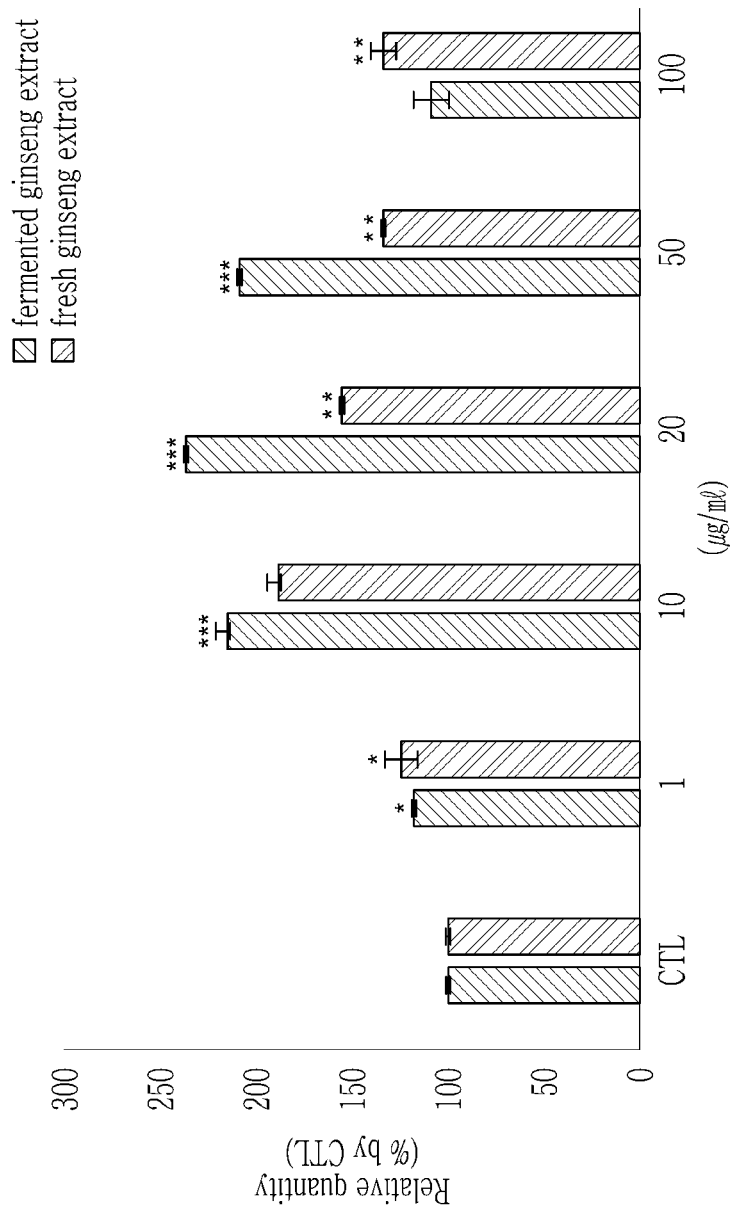
FIG. 5 is a graph showing results of VEGF-C cytokine analysis of the fermented ginseng extract in keratinocytes.
Figure 6:
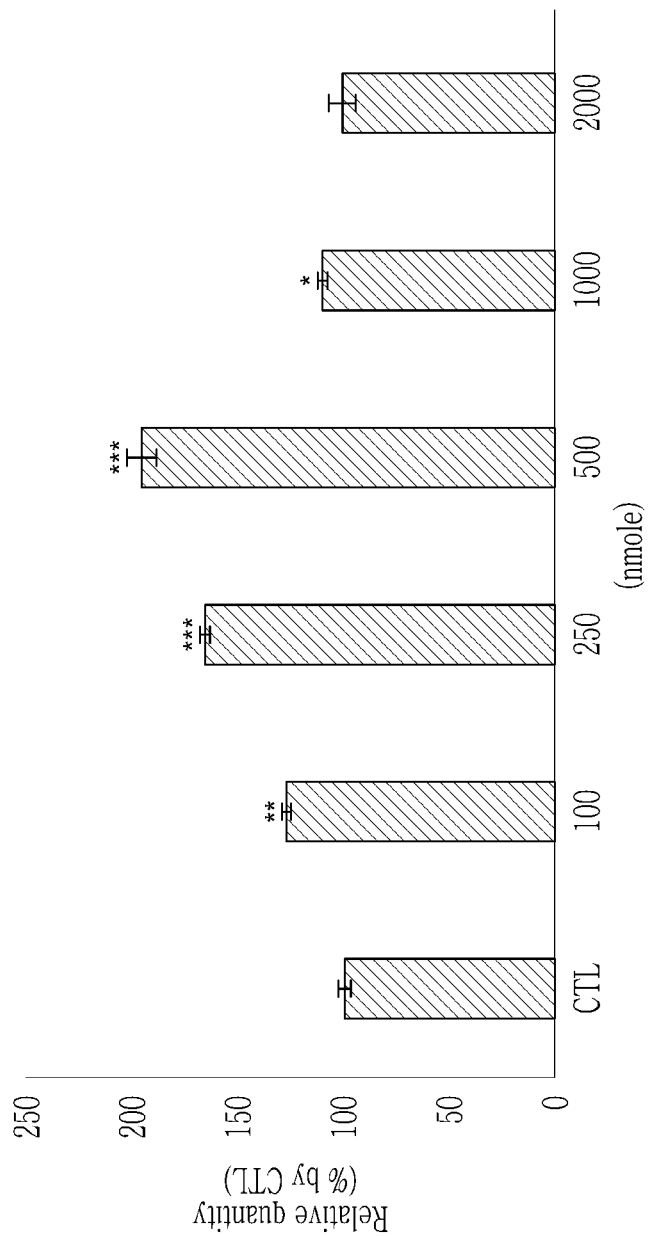
FIG. 6 is a graph showing results of VEGF-C cytokine analysis of the compound represented by Chemical Formula 1-1 in keratinocytes.

Normal human epidermal keratinocytes were cultured in 6 well plates for 24 hours, while treated with DMSO as a control group (reference; 100%), treated with the fermented ginseng extract of the preparation example and the compound represented by Chemical Formula 1-1 (Sigma-Aldrich Co., Ltd.) at each concentration of 1, 10, 20, 50 and 100 μg/ml and at each concentration of 100, 250, 500, 1000, and 2000 nmoles, cultured for 48 hours, and then measured with respect to production and activity of VEGF-C through VEGF-C cytokine analysis by using VEGFC Human ELISA Kit (ThermoFisher Scientific, U.S.A.) according to a manual, and the results are shown in FIGS. 5 and 6.

Referring to FIGS. 5 and 6, the compound represented by Chemical Formula 1-1 and the fermented ginseng extract including the same more improved the production and activity of VEGF-C than the control group.

Experimental Example 4: Preparation of Skin External Composition

Cosmetic compositions usable as an external skin preparation according to Example 1 and Comparative Example 1 (fresh ginseng extract; Silla University) were prepared with the composition and content shown in Table 1 below. The cosmetic compositions were prepared by adding purified water in a balance amount to reach a total amount of 100 wt %, when summed with weights of the other components.

TABLE 1

(unit: ppm)

|  | Example 1 | Comparative Example 1 |
|---|---|---|
| Purified water | balance | balance |
| EDTA-2Na | 0.05 | 0.05 |
| Lauric acid | 5 | 5 |
| Myristic acid | 7 | 7 |
| Palmitic acid | 1 | 1 |
| KOH | 7.9 | 7.9 |
| Guar hydroxypropyl trimonium chloride | 0.5 | 0.5 |
| Polyquaternium-7 | 3.0 | 3.0 |
| Fermented ginseng extract of Preparation Example | 5.0 | — |
| Fresh ginseng extract | — | 5.0 |
| Disodium cocoamphodiacetate | 1.0 | 1.0 |

After selecting 30 women having edema in lower leg calves over the age of 50 and instructing them to apply the compositions according to Example 1 and Comparative Example 1 on the swollen lower leg calf area twice a day for 7 consecutive days, each of them was asked to measure i) change in weight (using a scale), ii) change in circumference length of the calf where it was the most swollen, and iii) state of swelling (examined with the naked eye), and the results are shown in Table 2.

TABLE 2

|  | Example 1 | Comparative Example 1 |
|---|---|---|
| Weight (0 days) (kg) | 61 | 60 |
| Weight (7 days) (kg) | 59 | 61 |
| Calf circumference (0 days) (cm) | 40 | 40 |
| Calf circumference (7 days) (cm) | 39 | 40 |
| Edema condition | relieved | no change |

From Table 2, it can be confirmed that when the skin external composition according to an embodiment is prescribed, the edema condition is relieved within a week compared to the case where it is not.

Although the preferred embodiments of the present invention have been described in detail, the scope of the present invention is not limited thereto, and various modifications and improvements by those skilled in the art using the basic concept of the present invention defined in the following claims are also within the scope of the invention.

What is claimed is:

1. A reelin and/or VEGF-C production and activation promoter comprising an extract of rolled and anaerobically fermented ginseng as an active ingredient to promote reelin and/or VEGF-C production and activation,
wherein the extract is obtained by a process comprising:
washing a fresh ginseng, which is non-dried raw ginseng; repeatedly rubbing the washed ginseng with a physical force to obtain the rolled ginseng in which cell tissues and cell walls are broken; cutting and/or crushing the rolled ginseng into pieces; naturally fermenting the cut and/or crushed rolled ginseng under anaerobic conditions without an inoculation of microorganisms; drying the anaerobically fermented ginseng; placing the dried anaerobically fermented ginseng in 50% to 80% ethanol for 1 to 5 hours at 50° C. to 80° C. for extraction, and removing the extraction solvent to obtain the extract, and wherein the extract includes a compound of the following chemical formula 1-1:

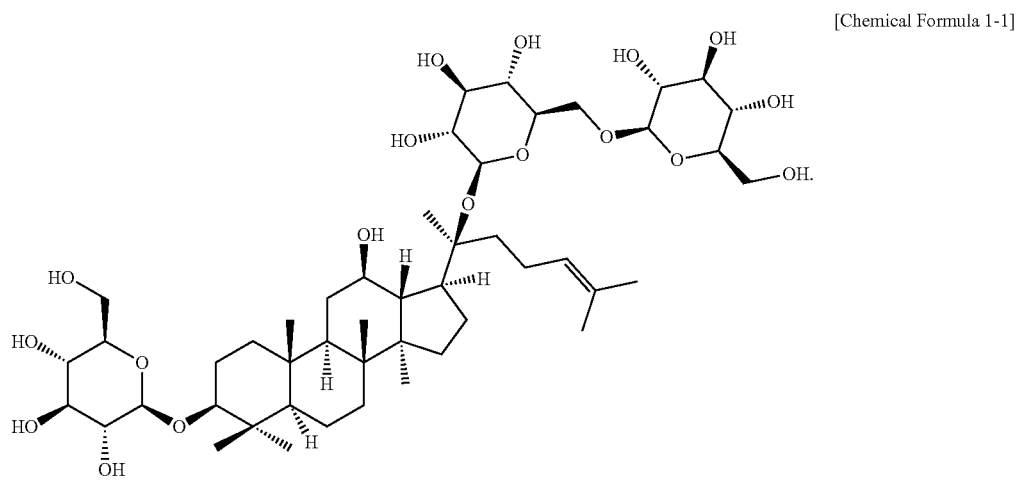

[Chemical Formula 1-1]

2. The reelin and/or VEGF-C production and activation promoter of claim 1, wherein the extract of rolled and anaerobically fermented ginseng is included in a concentration range of about 1 μg/ml to about 100 mg/ml based on a total amount of the reelin and/or VEGF-C production and activation promoter.

3. A skin external composition for improving lymphedema or swelling caused by an abnormal formation of lymphatic vessel, dysfunction of lymphatic vessels or both, comprising an extract of rolled and anaerobically fermented ginseng as an active ingredient to promote production or activation of reelin and/or VEGF-C and a cosmetically acceptable medium or base, wherein the extract is obtained by a process comprising: washing a fresh ginseng, which is non-dried raw ginseng; repeatedly rubbing the washed ginseng with a physical force to obtain the rolled ginseng in which cell tissues and cell walls are broken; cutting and/or crushing the rolled ginseng into pieces; naturally fermenting the cut and/or crushed rolled ginseng under anaerobic conditions without an inoculation of microorganisms; drying the anaerobically fermented ginseng; placing the dried anaerobically fermented ginseng in 50% to 80% ethanol for 1 to 5 hours at 50° C. to 80° C. for extraction, and removing the extraction solvent to obtain the extract, and wherein the extract includes a compound of the following chemical formula 1-1:

[Chemical Formula 1-1]
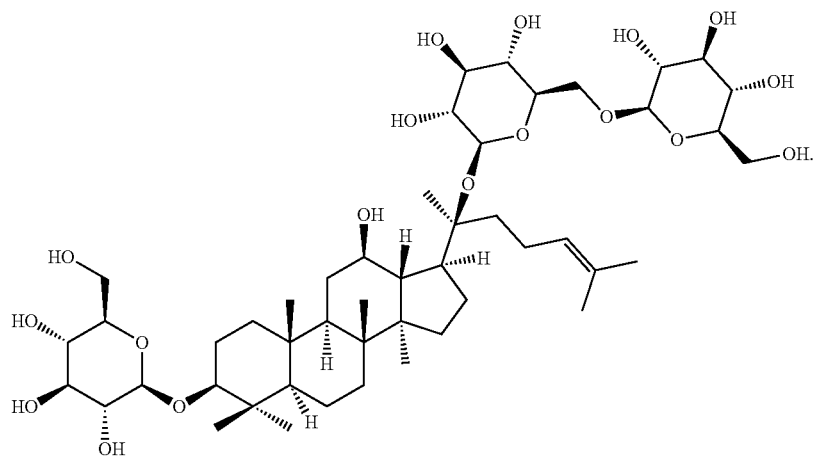
* * * * *